US006255099B1

United States Patent
Duttweiler et al.

(10) Patent No.: US 6,255,099 B1
(45) Date of Patent: Jul. 3, 2001

(54) HIGH-YIELD DUAL-BUFFERED BACTERIAL GROWTH MEDIUM

(75) Inventors: Harry M. Duttweiler, Ruidoso, NM (US); David S. Gross, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/505,497

(22) Filed: Feb. 17, 2000

(51) Int. Cl.[7] .................................................. C12N 1/20
(52) U.S. Cl. .................. 435/253.6; 435/243; 435/252.8; 435/320.1; 435/404
(58) Field of Search .................................. 435/404, 243, 435/253.6, 252.8, 320.1

(56) References Cited

U.S. PATENT DOCUMENTS

| | | | |
|---|---|---|---|
| 4,071,412 | 1/1978 | Eisenberg et al. | 195/102 |
| 4,656,132 | 4/1987 | Ben-Bassat et al. | 435/68 |
| 4,894,334 | 1/1990 | Ben-Bassat et al. | 435/69.1 |
| 5,223,418 | 6/1993 | Arcuri et al. | 435/172.3 |
| 5,658,790 | 8/1997 | Gautsch | 435/404 |

OTHER PUBLICATIONS

Computer CNBN Abstract 12(17):020506 Merck Sciential Review (Apr. 1996) 12, 24.*
Ausubel, F.M. et al., Current Protocols in Molecular Biology, John Wiley & Sons, vol. 1, pp. 1.1.1–1.1.3 (1995).
Doelle, H.W. et al., "Regulation of glucose metabolism in bacterial systems," *Adv. Biochem. Eng.* vol. 23, pp. 1–35 (1982).
Duttweiler, H.M. et al., "Bacterial Growth Medium that Significantly Increases the Yield of Recombinant Plasmid," *BioTechniques* vol. 24, No. 3, pp. 438–444 (1998).
Kleman, G.L. and W. R. Strohl, "Developments in high cell density and high productivity microbial fermentation," *Current Opinion in Biotechnology* vol. 5, pp. 180–186 (1994).
Luli, G.W. and W. R. Strohl, "Comparison of Growth, Acetate Production, and Acetate Inhibition of *Escherichia coli* Strains in Batch and Fed–Batch Fermentations," *Appl. Environ. Microbiol.* vol. 56, No. 4, pp. 1004–1011 (1990).
Sambrook, J., E. F. Fritsch, and R. Maniatis, Molecular Cloning: A Laboratory Manual, Second Edition, CSH Laboratory Press, pp. 1.21–1.23, A.1–A.3 (1989).
Tartof, K.D., and C. A. Hobbs, "Improved Media for Growing Plasmid and Cosmid Clones," *Bethesda Res. Lab. Focus* vol. 9 No. 2, pp. 12 (1987).
Zimmerman, H., "5'–Nucleotidase: molecular structure and functional aspects," *Biochemical Journal* vol. 285, pp. 345–365 (1992).

* cited by examiner

*Primary Examiner*—Herbert J. Lilling
(74) *Attorney, Agent, or Firm*—Bonnie J. Davis; John H. Runnels

(57) ABSTRACT

A novel growth medium called "H15" is disclosed that supports much higher *E. coli* cell densities and, concomitantly, a much higher yield of plasmid than previously reported for small-scale applications. The high-yield growth medium contains two buffers with different pKa values and an additional nucleotide source. On a unit volume basis, *E. coli* cultures grown in this medium consistently produce 5–10 times, and sometimes up to 30 times, more recombinant plasmid than in conventional rich media, paralleling the increase in cell density. This phenomenon is independent of *E. coli* host strain, DNA insert size and plasmid copy number. H15 medium is economical and high yields can be achieved using standard research laboratory equipment.

34 Claims, 1 Drawing Sheet

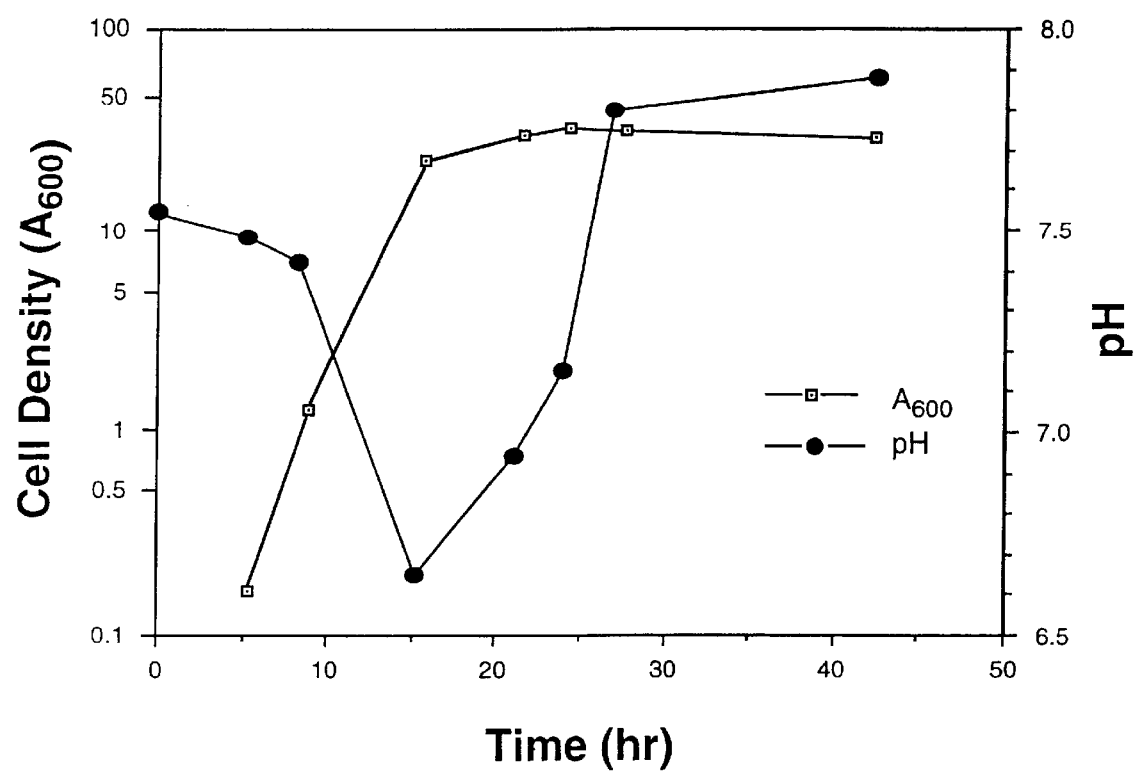

HIGH-YIELD DUAL-BUFFERED BACTERIAL GROWTH MEDIUM

The benefit of the Feb. 23, 1999 filing date of provisional application nnnnn (which was a conversion of nonprovisional application 09/255,936) is claimed under 35 U.S.C. § 119(e).

The development of this invention was partially funded by the Government under grant no. GM45842 from the National Institutes of Health. The Government has certain rights in this invention.

The present invention pertains to a high-yield, dual-buffered growth medium that supports the growth of bacterial cell cultures at higher densities than those achieved by conventional rich media.

The propagation of recombinant DNA in *E. coli* is a ubiquitous and necessary prerequisite for almost any endeavor in molecular biology, from cloning and sequencing of genes to ectopic expression of proteins. Many vectors have been used for this purpose, including plasmids, cosmids, and bacterial artificial chromosomes (BACs). Rich media such as Luria-Bertani (LB) broth, "Superbroth," and "Terrific Broth" (TB) have been developed to enhance the normal growth of transformed bacterial cells. See generally, F. M. Ausubel et al., Current Protocols in Molecular Biology, John Wiley & Sons, pp. 1.1.1–1.1.3 (1997); J. Sambrook, E. F. Fritsch, and R. Maniatis, Molecular Cloning: A Laboratory Manual, $2^{nd}$ ed., CSH Laboratory Press, pp. 1.21–1.23, A1–A3 (1989); K. D. Tartof and C. A. Hobbs, "Improved Media for Growing Plasmid and Cosmid Clones," *Bethesda Res. Lab. Focus* vol. 9, p. 12 (1987). LB and its derivatives are the most commonly used, possibly because more complex recipes improve yield only slightly. In most cases, the moderate increase in yield does not justify the added time and effort to make the more complex media.

Cell density in liquid culture is limited by certain byproducts of metabolism. Growth of *E. coli* on excess glucose under aerobic conditions causes formation of acidic by-products, of which acetate is the most predominant. See H. W. Doelle et al., "Regulation of glucose metabolism in bacterial systems," *Adv. Biochem. Eng.* vol. 23, pp. 1–35 (1982); G. W. Luli and W. R. Strohl, "Comparison of growth, acetate production, and acetate inhibition of *Escherichia coli* strains in batch and fed-batch fermentations, " *Appl. Environ. Microbiol.* vol. 56, pp. 1004–1011 (1990)). High acetate concentrations can severely inhibit cell growth, genetic stability, and recombinant protein production. (G. W. Luli and W. R. Strohl, *Appl. Environ. Microbiol.* vol. 56, pp. 1004–1011 (1990)). While high cell density techniques have been developed for fed-batch fermentations (reviewed in G. L. Kleman and W. R. Strohl, "Developments in high cell density and high productivity microbial fermentation," *Current Opinion in Biotechnology* vol. 5 pp. 180–186 (1994)), none have been developed for small-scale applications appropriate for the typical research laboratory.

U.S. Pat. Nos. 4,656,132 and 4,894,334 disclose a process for improving the yield of heterologous protein produced by recombinant bacteria by supplementing the nutrient medium with a water soluble alcohol and an amino acid mixture during the terminal phase of cultivation.

U.S. Pat. No 5,223,418 discloses a method of improving the yield of heterologous proteins produced by recombinant *Streptomyces lividans* by using a complex nutrient medium supplemented with high concentrations of casamino acids (1–5%) and glucose (up to 3%).

U.S. Pat. No. 5,658,790 discloses a method to prepare a cell culture medium by using unit dose packaging of a dry concentrate of the medium. The formulations contain a single buffer, Tris, to maintain a neutral pH. Alternative embodiments contain low concentrations of glucose (0.4%) and casamino acids (0.6%).

In addition to external sources of carbon, nitrogen, and energy, bacteria can utilize an external source of ribonucleosides. Ribonucleotides in the growth medium can be hydrolyzed by periplasmnic phosphatases, generating permeable ribonucleosides that can enter the cell and be used for RNA synthesis. (H. Zimmerman, "5'-Nucleotidase: Molecular Structure and Functional Aspects," *Biochemical Journal* vol. 285, pp. 345–365 (1992)).

No known prior culture medium has a dual-buffer system or adds a source of free ribonucleotides.

There is a long felt need by those practicing recombinant DNA techniques for a high efficiency, inexpensive growth medium that can support high bacterial cell densities and high yields of plasmid DNA or of recombinant protein using equipment available in an ordinary research laboratory.

We have discovered a novel growth medium that supports much higher bacterial cell densities and, concomitantly, a much higher yield of plasmid than has been previously reported for small-scale applications. The high-yield growth medium contains two buffers with different pKa values and optionally includes an additional nucleotide source. On a unit volume basis, *E. coli* cultures grown in this medium have consistently produced 5–10 times, and sometimes up to 30 times, more recombinant plasmid than was produced in conventional rich media, paralleling the increase in cell density. This phenomenon is independent of *E. coli* host strain, DNA insert size, and plasmid copy number. The medium is economical, and high yields can be achieved using standard research laboratory equipment.

BRIEF DESCRIPTION OF THE DRAWINGS

The FIGURE illustrates the relationship of cell density and pH of an *E. coli* culture grown on H15 medium as a function of time.

A preferred embodiment of the high-efficiency bacterial growth medium has been named "H15." This medium has supported *E. coli* growth to cell densities that were consistently 10-fold higher than those obtained in LB medium, and up to three times the densities possible in TB medium. More significantly, there was a 2- to 30-fold increase in the yield of plasmid DNA per unit volume of culture. H15 was formulated on the premise that in the presence of a sufficiently high level of nutrients and a strong buffering system, and in the absence of inhibiting concentrations of acetate, *E. coli* will grow to high densities.

A unique feature of the novel medium is its strong buffering capacity for both acidic and basic metabolites. Without wishing to be bound by this theory, it is believed that the unexpectedly high efficiency of this medium is largely due to control of both acidic and basic pH. The pH of the prepared medium should not exceed pH about 7.7 or the cells will grow poorly. However, if the starting pH is much below about 7.6, the cells do not rebound after the initial growth phase, resulting in a substantial reduction in yield. Two buffers with different pKa values are used to buffer both acidic and basic by-products, thereby maintaining the pH of the growth medium within an optimal range. In a preferred embodiment, MOPS (3-(N-morpholino)-propanesulfonic acid) having a pKa of 7.0 at 37° C. and Tris (tris-(hydroxymethyl)aminomethane) having a pKa of 7.8 at 37° C. were used to achieve the dual buffering effect. Cells growing in H15 exhibited biphasic growth, which suggests that the acidic and basic buffering capacity of the medium is used at two different stages of growth. (See the FIGURE)

The medium is also unique in including a high concentration of free RNA along with the stable enzyme RNase A to provide free ribonucleotides. Since a large portion of a bacterial cell comprises RNA, supplementing the growth medium with ribonucleotides, which are hydrolyzed to permeable ribonucleosides by periplasmic phosphatases, encourages growth. In a preferred embodiment, the RNA source is bulk RNA extracted from torula yeast, which is not much more expensive than ordinary yeast extract.

A third unique feature is that the medium allows the use of energy, carbon, and nitrogen sources at high concentrations that are only feasible because the medium is strongly buffered against both acidic and basic by-products of cell growth. A preferred embodiment contains 2% glucose, 5% yeast extract, and 1% casamino acids.

An important parameter is aeration of the cultures. Oxygenation helps prevent a fermentation-induced rapid pH drop. Thus, a preferred embodiment uses vigorous agitation of a baffled flask at least ten times the culture volume. Lowering the incubation temperature to 32–34° C., thereby lowering the oxygen uptake rate, may lessen the degree of aeration required.

DEFINITIONS

The term "casamino acids" as used herein refers to the acid hydrolysate of casein. An "effective amount" of a component of a bacterial growth medium is an amount that substantially enhances the growth of bacteria, or that substantially enhances DNA yield, as compared to an otherwise identical growth medium that lacks the component in question, or that contains an excessive amount of the component in question. The term "exponential phase" of bacterial growth as used herein refers to the period during which bacteria in culture are dividing rapidly and cell density of the culture increases many fold. The term "secondary phase" of bacterial growth as used herein refers to the period when the rate of cell division becomes slower than the initial rapid rate seen at the onset of the exponential growth phase; cell cultures are still growing during the secondary phase, albeit more slowly. The term "stationary phase" of bacterial growth as used herein refers to the stage following the secondary phase, at which the growth and death rates are balanced such that there is no net increase or decrease in number of live cells; a cell culture generally enters this phase when it has used up an essential nutrient of the culture medium or some byproduct of the organism has built up to an inhibitory level.

EXAMPLE 1

Materials and Methods Plasmids and *E. Coli* Strains.

The following plasmids were used in this study: pUC18 (J. Sambrook et al., (1989)); pGFP, jellyfish Green Fluorescent Protein cDNA cloned into a pUC19 derivative (Clontech Laboratories, Palo Alto, Calif., USA); pBluescript (Stratagene, LaJolla, Calif., USA); pRS306 (a pBluescript derivative) (R. S. Sikorski and P. Heiter, *Genetics* vol. 122, pp. 19–27 (1989)); p2L, a 78 bp yeast HSP82 promoter fragment subcloned into pSP65 (Promega, Madison, Wis., USA); pUTX20, 2.9 kb EcoRI fragment of the yeast HSP82 gene cloned into pBR322; p103, HSP82 EcoRI fragment cloned into a YIp5 derivative (S. Lee and D. S. Gross, *Mol. Cell. Biol.* Vol 13, pp. 727–738 (1993)); and pGST-ScHSF, 2.9 kb Pvu II-Xho I fragment of *S. cerevisiae* HSF1 cloned into the Sma I site of pGEX-2T (Pharmacia Biotech, Piscataway, N.J., USA) (A. M. Erkine et al., Mol. Cell. Biol. Vol. 16, p. 7004–7017 (1996)). The *E. coli* strains used were as follows: DH5α (as described by Sambrook et al., p.A.10, 1989); HB101 (as described by Sambrook et al., p. A.10, 1989); Sure (Strategene, La Jolla, Calif.), JM83 (as described by J. Messing, Methods Enzymol., vol. 101, pp. 20–78 (1983)), GM272 (from the Cold Spring Harbor Laboratory, Cold Spring Harbor, N.Y.).

Preparation of Media.

For 100 ml of H15 medium, 1 g of RNA (from torula yeast [#R-6625], Sigma Chemical Company, St. Louis, Mo., USA), 5 g yeast extract (Difco Laboratories, Detroit, Mich., USA), 1 g casamino acids (Difco), and 1 mg RNase A (Sigma) were added to 80 ml of distilled water. This solution was stirred vigorously in a 150 ml beaker until no longer cloudy (usually 15 minutes). Then, 5.23 g of 3-(N-morpholino)-propanesulfonic acid (MOPS)-free acid and 3.3 g of tris-(hydroxymethyl)aminomethane (Tris free base) were added. These two buffer salts were added simultaneously to avoid exposing the medium to an extreme pH. The solution was then stirred until the buffer salts dissolved. The pH was adjusted to 7.6 with concentrated HCl before the solution was sterilized by autoclaving. Finally, 10 ml of sterile 20% glucose was added; and the total volume of the solution was adjusted to 100 ml with distilled water. (Autoclaving MOPS in the presence of glucose produces unstable products which inhibit *E. coli* growth. If medium is to be used immediately, autoclaving is not normally necessary. Alternatively, the solution could be sterilized by filter sterilization or ionizing radiation, as described by Eisenberg etal., U.S. Pat. No. 4,071,412.) The composition of H15 is summarized in Table 1.

TABLE 1

Composition of H15 Growth Medium

| | |
|---|---|
| 1% | RNA |
| 5% | Yeast Extract |
| 1% | Casamino Acids |
| 2% | Glucose |
| 250 mM | MOPS |
| 272 mM | Tris |
| 10 µg/mL | RNase A |
| pH 7.6 adjusted with HCl | |

Other Growth Media Tested.

1. LB medium. The LB medium consisted of 1% (w/v) tryptone, 0.5% (w/v) yeast extract, and 170 mM NaCl, at pH 7.

2. TB medium. The TB medium consisted of 1.2% (w/v) tryptone, 2.4% (w/v) yeast extract, 55 mM glycerol, 17 mM $KH_2PO_4$, and 72 mM $K_2HPO_4$.

3. 2×YT medium. The YT medium consisted of 1.6% (w/v) tryptone, 1% (w/v) yeast extract, and 85 mM NaCl and pH 7.

4. SOC medium. The SOC medium consisted of 2% (w/v) tryptone, 0.5% (w/v) yeast extract, 8.5 mM NaCl, 2.5 mM KCl, 10 mM $MgCl_2$, and 20 mM glucose at pH 7.

All media were prepared as described in J. Sambrook, E. F. Fritsch, and T. Maniatis, Molecular Cloning: A Laboratory Manual, $2^{nd}$ ed. CSH Laboratory Press, pp. A.1–A.3 (1989).

Cell Cultivation and Plasmid Isolation.

*E. coli* cells were inoculated into 20 ml of LB, TB, SOC, 2×YT, or H15 and cultivated in baffled 300 ml Erlenmeyer flasks at 37° C., which were shaken vigorously (300 rpm) for 24–30 hours. Cells were harvested, washed twice with distilled water, and DNA was isolated using the SDS alkaline lysis method (Sambrook et al., 1989). Washing cells was important because H15 medium, which is strongly buffered, should be completely removed for the alkaline lysis method to be effective. DNA yields were quantitated using the Hoechst 33258 fluorescence enhancement assay described in C. Labarca and K. Paigen "A Simple, Rapid, and Sensitive DNA Assay Procedure," *Analytical Biochemistry* vol. 102, pp. 344–352 (1980).

EXAMPLE 2

Growth of *E. Coli* in H15 Medium

One large loopful of GM272 cells (transformed with plasmid pUTX20) was used to inoculate 20 ml of H15 medium to which ampicillin had been added to a final concentration of 75 $\mu$g/ml. Culture was grown in a 300 ml baffled Erlenmeyer flask at 37° C. shaken at 300 rpm. Aliquots were removed, diluted, and pH and cell density measurements taken. The initial *E. coli* growth phase in H15 medium was exponential. This was followed by a second, slower growth phase (see FIGURE). An optimal carbon and energy source for *E. coli*, as for many organisms, is glucose (see H. W. Doelle et al., *Adv. Biochem. Eng.* vol. 23, pp. 1–35 (1982)). As H15 contains 2% glucose, the cells preferentially used this carbon source in the initial phase of growth. However, growth on glucose under aerobic conditions produces acidic byproducts. See H. W. Doelle et al., *Adv. Biochem. Eng.* vol. 23, pp. 1–35 (1982); G. W. Luli and W. R. Strohl, *Appl. Environ. Microbiol.* vol. 56, pp. 1004–1011 (1990)). When the acidic byproducts drop the pH much below 6.0, the cells enter a stationary phase and stop growing. To prevent this, H15 medium contains 250 mM MOPS, having a pKa of 7.0 at 37° C. The medium also contains 270 mM Tris to buffer the solution to pH 7.6. Thus, as the bacteria grew and excreted acidic byproducts into the H15 medium, the entire buffering capacity of MOPS would have to be titrated before the pH dropped sufficiently to inhibit growth. At an initial concentration of 2% glucose, the cells depleted the medium of the sugar at an approximate pH of 6.5, which is the lower limit of the buffering range of MOPS.

After the initial exponential growth phase, the cells used other compounds in the medium as carbon and energy sources, including acetate and amino acids. The primary source of energy then became the yeast extract. Growth during this phase produced more basic byproducts than acidic. This is seen in the FIGURE, where the pH started to rise as the cells continued to grow. During this secondary phase, Tris, which has a pKa of 7.8 at 37° C., served as the primary buffering agent. When the pH of the medium approached pH 8, the cells entered a stationary phase and ceased growth.

EXAMPLE 3

Performance of H15 Medium Using Different *E. Coli* Strains

Five commonly used *E. coli* strains, carrying derivatives of the pMB1 plasmid with inserts of varying sizes, were tested for their ability to grow in H 15. As summarized in Table 2, it is clear that for each strain/plasmid combination, the cultures grew to dramatically greater densities in H15 than in LB, TB, or SOC growth media. Thus, the beneficial effect of H15 medium on cellular growth was neither strain-specific nor dependent on plasmid size.

TABLE 2

Effect of Growth Media on the Optical Density of Stationary Cultures

| | $A_{600}$ | | |
|---|---|---|---|
| Plasmid (*E. coli* strain) | LB | TB | H15 |
| pUC18 (JM83) | 3.6 | 24.5 | 34.8 |
| pGFP (Sure) | 3.4 | 15.3 | 36.4 |
| pBluescript (DH5α) | 2.7 | 14.1 | 41.9 |
| pRS306 (DH5α) | 3.1 | 18.5 | 46.9 |
| p2L (HB101) | 4.7 | 24.9 | 47.7 |
| pUTX20 (GM272) | 3.7 | 14.9 | 42.9 |
| p103 (DH5α) | 10[a] | N.D.[b] | 35.1 |

[a]Plasmid p103 in *E. coli* strain DH5α was grown in SOC medium instead of LB
[b]N.D. = not determined

EXAMPLE 4

Plasmid Yield Using H15 Medium

To test whether plasmid yield paralleled the increase in saturation densities seen in Example 3, a small aliquot (250 $\mu$l) of each culture was harvested and plasmid DNA was extracted. Strikingly, *E. coli* grown in H15 gave rise to DNA yields that were 6 to 30 times the yields of the same strains grown in LB (Table 3). H15 also significantly out-performed TB (2- to 6-fold). Noteworthy was the fact that the increase in DNA yield was similar for plasmids that are known to be maintained at a relatively low copy number (e.g., p103 and pUTX20, which showed a 10- to 13-fold increase) and those known to be maintained at high copy number (e.g., pUC18, which showed a 12-fold increase). Moreover, in nearly every case the increase in DNA yield was as large as the increase in cell density, and sometimes exceeded it.

TABLE 3

Plasmid Yield From Stationary Cultures

| | | $\mu$g of plasmid DNA per mL of *E. coli* culture[a] | | |
|---|---|---|---|---|
| Plasmid | Size | LB | TB | H15 |
| pUC18 | 2.7 kb | 3.8 | 14.2 | 44.9 |
| pGFP | 3.3 kb | 3.4 | 10.9 | 44.8 |
| pBluescript | 3.0 kb | 6.8 | 26.7 | 48.0 |
| pRS306 | 4.4 kb | 5.6 | 18.0 | 33.6 |
| p2L | 3.1 kb | 3.7 | 17.6 | 109.0 |
| pUTX20 | 7.3 kb | 1.0 | 5.4 | 12.6 |
| p103 | 8.4 kb | 1.2[b] | N.D.[c] | 12.6 |
| pGST-ScHSF | 7.8 kb | 10.0[b] | N.D. | 87.5 |

[a]Samples were quantitated using the Hoechst 33258 fluorescence enhancement assay.
[b]Plasmids p103 and pGST-ScHSF were grown in SOC medium and 2× YT medium, respectively, instead of LB medium.
[c]N.D. = not determined

EXAMPLE 5

Integrity of Plasmids Grown in H15

The integrity of the DNA of plasmids grown in various media was compared. Plasmid p2L was propagated in *E. coli* strain HB101 growing in LB, TB, or H15 medium. Intact plasmid DNA extracted from a 25 $\mu$l aliquot of LB, TB, or H15 cell cultures was electrophoresed on a 1% agarose gel and then stained with ethidium bromide. Based on the known migration patterns of p2L DNA in 1% agarose, it was determined that plasmid isolated from *E. coli* grown in H 15 exhibited a topoisomer distribution similar to that of plasmid isolated from either LB or TB cultures. In all three cases, the predominant species appeared to be supercoiled, while a minor proportion appeared to be in the relaxed circular or linear form. Moreover, DNA of plasmid pRS306 propagated in E. coli strain DH5α grown in H15 was cut efficiently by a variety of restriction enzymes. Thus, despite growing to a substantially higher cell density in H 15 medium than in traditional media, E. coli physiology was not appreciably altered with respect to plasmid DNA replication.

EXAMPLE 6
Role of Individual Medium Components in Enhancing Plasmid Yield

To demonstrate the role of each component of the medium, variations of H15 were prepared in which one of the components was either omitted or altered. Table 4 lists the effect of these alterations on the growth of E. coli strain JM83 transformed with plasmid pUC 18. Omitting RNA, RNase A, or casamino acids had a similar outcome: the cultures experienced a long lag phase and required at least 48 hr to reach stationary phase, but eventually reached a cell density comparable to that of complete H15. However, in each case the yield of plasmid DNA was lower. The relatively mild effect of omitting casamino acids may be attributable to the fact that hydrolyzed protein and amino acids are abundant in yeast extract. Omission of RNase A caused the smallest decrease in plasmid DNA yield, even though it did delay the transition to stationary phase, indicating that addition of RNase A is an important but not essential element in the effectiveness of H15. If MOPS buffer was omitted (H15 titrated to pH 7.6 with HCl), the culture reached a much lower final density in the stationary phase (measured as $A_{600}$) and showed a 76% drop in plasmid yield. With MOPS omitted, the pH of the stationary phase medium was 5.0. A similar, although less severe, outcome was seen when Tris was omitted (55% drop in plasmid yield). A nearly 60% reduction in plasmid yield was seen when the glucose concentration was increased to 3%, presumably stemming from excess acetate production. Thus, altering the concentration of any component outside its acceptable range reduces the efficacy of H15 as a bacterial growth medium.

It should be noted that even when various ingredients are omitted or modified, yields of plasmid DNA in modified H15 were still higher than those achieved in LB broth (see Table 3). Only the omission of MOPS buffer led to a lower yield of plasmid DNA (10.8 μg DNA/mL) than the yield obtained using TB medium (14.2 μg DNA/mL, see Table 3). All other omissions or modifications still resulted in DNA yields higher than those obtained using TB medium. The dramatic effect of omitting MOPS provides evidence of the importance of dual buffering in achieving the high yields seen with H15 medium.

TABLE 4

Effect of Altering H15 Composition on Cell Density and Plasmid Yield[a]

| Alteration | $A_{600}$ | μg of plasmid DNA per mL of culture |
|---|---|---|
| None | 34.8 | 44.9 |
| −RNA[b] | 27.0 | 23.2 |
| −Casamino Acids[b] | 30.4 | 32.4 |
| +1% glucose (= total 3% glucose) | 21.0 | 19.0 |
| −MOPS | 13.3 | 10.8 |
| −Tris Base | 28.9 | 20.3 |
| −RNase A[b] | 29.3 | 38.1 |

[a]Experiment used E. coli strain JM83 transformed with plasmid pUC18
[b]Required at least 48 h to reach saturation; all other compositions required 24–30 h.

One of ordinary skill in the art can easily practice this invention using materials commonly available in laboratories. Routine modifications of the embodiments disclosed herein can be carried out so long as they maintain the high efficiency of H15 medium. Preferred concentrations of the constitutents of H15 medium are in the following ranges:
a) RNA: from about 0.5% to about 2.0%;
b) Yeast extract: from about 2% to about 8%;
c) Casamino acids: from about 0.5% to about 2.0%;
d) Glucose: from about 1.5% to about 2.5%;
e) MOPS: from about 220 mM to about 280 mM;
f) Tris base: from about 225 mM to about 325 mM;
g) RNase A: from about 1.5 μg/mL to about 15.0 μg/mL.

Buffers of similar pKa and buffering capacity may be substituted for the combination of Tris and MOPS. An alternative buffer system would be a phosphate buffered system comprising from about 0.1 M to about 0.5 M dibasic sodium phosphate and from about 0.1 M to about 0.5 M monobasic sodium phosphate, a combination having maximal buffering capacity between about pH 5.8 to about pH 8.0 at 37° C. Alternatives to MOPS would comprise buffers having maximal buffering capacity from about pH 6.6 to about pH 7.8 at 37° C., including but not limited to, an imidazole-HCl buffer and an 2,4,6-trimethylpyridine-HCl buffer. Alternatives to Tris free base would comprise buffers having maximal buffering capacity from about pH 7.1 to about pH 8.9 at 37° C., including but not limited to, a HEPES (4-(2-hydroxyethyl)-1-piperazineethane-sulfonic acid) buffer and a TRICINE (N-[2-Hydroxy-1,1-bis (hydroxymethyl)-ethyl]glycine buffer.

Sources of energy, carbon, nitrogen, ribonucleosides and trace nutrients may be substituted so long these substitutions or modifications maintain high efficiency, ease of preparation, and an acceptable cost. Ingredient concentrations may be modified within an acceptable range so long as the desired properties of the present invention are preserved.

On the basis of DNA yield, H15 is comparable in expense to conventional media. One of the most significant benefits of H 15 for the typical research laboratory is that it obviates the need for floor-model centrifuges and rotors sufficiently large to accommodate 0.5–1.0 liter bottles, since as much as 1 mg of plasmid DNA can be harvested from as little as 20 ml of culture. Thus, plasmid "maxipreps" can be conducted using relatively inexpensive benchtop centrifuges and rotors.

A bacterial growth medium with extremely high performance such as H15 has a wide variety of applications. It could be used in the preparation of plasmids, cosmids, and BACs (bacterial artificial chromosomes) for research use. Enhanced yields of DNA could allow culture flasks, centrifuge rotors, and other equipment to be scaled back in size, with a concomitant savings in cost. Such a medium is of special value to laboratories working on genome projects, which are heavily dependent on automation, and could be adapted for use with, for example, 96-well microtiter dishes, permitting simultaneous amplification of a large number of different plasmids. Adoption of such a medium can greatly increase productivity without the necessity of expensive equipment upgrades.

Additionally, the enhanced bacterial growth seen with H15 growth medium may also be valuable in the production of recombinant protein, either as an intracellular or secreted protein product, obviating the necessity for large volume purification. Bacteria cells comprising at least one exogenous gene for a recombinant protein could be grown at high density in the H15 growth medium and then the recombinant protein could be extracted from the bacteria or the medium following the secondary phase of bacterial growth.

The complete disclosures of all references cited in this specification are hereby incorporated by reference. Also incorporated by reference is the complete disclosure of the following paper: H. M. Duttweiler and D. S. Gross, "Bacterial Growth Medium that Significantly Increases the Yield of Recombinant Plasmid," *BioTechniques* vol. 28, pp. 438–444 (1998). In the event of an otherwise irreconcilable conflict, however, the present specification shall control.

We claim:

1. A dual-buffer bacterial growth medium comprising:
   (a) an effective amount of a first buffer having a pKa between about 6.6 and about 7.5;
   (b) an efective amount of a second buffer having a pKa between about 7.5 and about 8.0;
   (c) an effective amount of free RNA;
   (d) an effective amount of an RNase enzyme; and
   (e) an effective amount of bacterial nutrients; wherein:
   (f) the pH of said medium is about 7.6 to about 7.7; and wherein:
   (g) the medium supports a signficantly higher density growth of bacterial cell cultures over time than either a single-buffer growth medium or a dual-buffer growth medium outside the pH range of about 7.6 to about 7.7.

2. A bacterial growth medium as recited in claim 1, wherein the components of said medium are in aqueous solution.

3. A bacterial growth medium as recited in claim 1, wherein said medium comprises:
   (a) between about 5 and about 20 parts RNA by weight;
   (b) between about 20 and about 80 parts yeast extract by weight;
   (c) between about 5 and about 20 parts casamino acids by weight;
   (d) between about 15 and about 25 parts glucose by weight;
   (e) between about 46 parts and about 59 parts 3-(N-morpholino)-propanesulfonic acid;
   (f) between about 27 parts and about 40 parts tris-(hydroxymethyl)aminomethane; and
   (g) between about 0.0015 and about 0.015 parts RNase A by weight.

4. A bacterial growth medium as recited in claim 3, wherein said medium comprises about 10 parts RNA by weight.

5. A bacterial growth medium as recited in claim 3, wherein said medium comprises about 50 parts yeast extract by weight.

6. A bacterial growth medium as recited in claim 3, wherein said medium comprises about 10 parts casamino acids by weight.

7. A bacterial growth medium as recited in claim 3, wherein said medium comprises about 20 parts glucose by weight.

8. A bacterial growth medium as recited in claim 3, wherein said medium comprises about 52.3 parts 3-(N-morpholino)-propanesulfonic acid by weight.

9. A bacterial growth medium as recited in claim 3, wherein said medium comprises about 42.95 parts tris-(hydroxymethyl)aminomethane by weight.

10. A bacterial growth medium as recited in claim 3, wherein said medium comprises about 0.01 parts RNase A by weight.

11. A bacterial growth medium as recited in claim 3, additionally comprising water in an amount sufficient to bring the total volume to 1000 parts.

12. A method comprising growing bacteria in a bacterial growth medium as recited in claim 11, wherein during both the exponential and the secondary phases of bacterial growth the pH is always within the range between about 6.5 and about 8.0.

13. A method comprising growing bacteria in a bacterial growth medium as recited in claim 11, wherein the bacteria acidifies the medium, the first buffer preventing the pH dropping below about 6.5; then the bacteria excretes basic metabolites, the second buffer preventing the pH rising above about 8.0; whereby the pH is maintained between about 6.5 and 8.0; thereby enhancing growth of the bacteria.

14. A method as recited in claim 12, additionally comprising aerating the medium during bacterial growth.

15. A method as recited in claim 12, wherein the bacteria comprise at least one exogenous plasmid, additionally comprising the step of extracting plasmid DNA from the bacteria following the secondary phase of bacterial growth.

16. A method as recited in claim 12, wherein the bacteria comprise at least one exogenous gene encoding a recombinant protein, additionally comprising the step of extracting recombinant protein from the bacteria or the medium following the secondary phase of bacterial growth.

17. A dual-buffer bacterial growth medium comprising:
   (a) an effective amount of a first buffer having a pKa between about 6.6 and about 7.5;
   (b) an effective amount of a second bluffer having apKa between about 7.5 and about 8.0;
   (c) an effective amount of free RNA; and
   (d) an effective amount of bacterial nutrients; wherein:
   (e) the pH of said medium is about 7.6 to about 7.7; and wherein:
   (f) the medium supports a significanty higher density growth of bacterial cell cultures over time than either a single-buffer growth medium or a dual-buffer growth medium outside the pH range of about 7.6 to about 7.7.

18. A bacterial growth medium as recited in claim 17, wherein the components of said medium are in aqueous solution.

19. A bacterial growth medium as recited in claim 17, wherein said medium comprises:
   (a) between about 20 and about 80 parts yeast extract by weight;
   (b) between about 5 and about 20 parts casamino acids by weight;
   (c) between about 15 and about 25 parts glucose by weight;
   (d) between about 46 parts and about 59 parts 3-(N-morpholino)-propanesulfonic acid;
   (e) between about 27 parts and about 40 parts tris-(hydroxymethyl)aminomethane; and
   (f) between about 5 and a bout 20 parts RNA by weight.

20. A bacterial growth medium as recited in claim 19, additionally comprising water in an amount sufficient to bring the total volume to 1000 parts.

21. A method comprising growing bacteria in a bacterial growth medium as recited in claim 20, wherein during both the exponential and the secondary phases of bacterial growth the pH is always within the range between about 6.6 and about 8.0.

22. A method comprising growing bacteria in a bacterial growth medium as recited in claim 20, wherein the bacteria acidifies the medium, the first buffer preventing the pH dropping below about 6.5; then the bacteria excretes basic metabolites, the second buffer preventing the pH rising above about 8.0; whereby the pH is maintained between about 6.5 and 8.0; thereby enhancing growth of the bacteria.

23. A method as recited in claim 21, additionally comprising aerating the medium during bacterial growth.

24. A method as recited in claim 21, wherein the bacteria comprise at least one exogenous plasmid, additionally comprising the step of extracting plasmid DNA from the bacteria following the secondary phase of bacterial growth.

25. A method as recited in claim 21, wherein the bacteria comprise at least one exogenous gene encoding a recombinant protein, additionally comprising the step of extracting recombinant protein from the bacteria or the medium following the secondary phase of bacterial growth.

26. A dual-buffer bacterial growth medium comprising:
 (a) an effective amount of a first buffer having a pKa between about 6.6 and about 7.5;
 (b) an effective amount of a second buffer having a pKa between about 7.5 and about 8.0; and
 (c) an effective amount of bacterial nutrients; wherein:
 (d) the pH of said medium is about 7.6 to about 7.7; and wherein:
 (e) the medium supports a significantly higher density growth of bacterial cell cultures over time than either a single-buffer growth medium or a dual-buffer growth medium outside the pH range of about 7.6 to about 7.7.

27. A bacterial growth medium as recited in claim 26, wherein the components of said medium are in aqueous solution.

28. A bacterial growth medium as recited in claim 26, wherein said medium comprises:
 (a) between about 20 and about 80 parts yeast extract by weight;
 (b) between about 5 and about 20 parts casamino acids by weight;
 (c) between about 15 and about 25 parts glucose by weight;
 (d) between about 46 parts and about 59 parts 3-(N-morpholino)-propanesulfonic acid; and
 (e) between about 27 parts and about 40 parts tris-(hydroxymethyl)aminomethane.

29. A bacterial growth medium as recited in claim 28, additionally comprising water in an amount sufficient to bring the total volume to 1000 parts.

30. A method comprising growing bacteria in a bacterial growth medium as recited in claim 29, wherein during both the exponential and the secondary phases of bacterial growth the pH is always within the range between about 6.6 and about 8.0.

31. A method comprising growing bacteria in a bacterial growth medium as recited in claim 29 wherein the bacteria acidifies the medium, the first buffer preventing the pH dropping below about 6.5; then the bacteria excretes basic metabolites, the second buffer preventing the pH rising above about 8.0; whereby the pH is maintained between about 6.5 and 8.0; thereby enhancing growth of the bacteria.

32. A method as recited in claim 30, additionally comprising aerating the medium during bacterial growth.

33. A method as recited in claim 30, wherein the bacteria comprise at least one exogenous plasmid, additionally comprising the step of extracting plasmid DNA from the bacteria following the secondary phase of bacterial growth.

34. A method as recited in claim 30, wherein the bacteria comprise at least one exogenous gene encoding a recombinant protein, additionally comprising the step of extracting recombinant protein from the bacteria or the medium following the secondary phase of bacterial growth.

* * * * *